United States Patent [19]

Meulien

[11] Patent Number: 5,521,070

[45] Date of Patent: May 28, 1996

[54] DNA SEQUENCE CODING FOR HUMAN FACTOR IX OR A SIMILAR PROTEIN, EXPRESSION VECTOR, TRANSFORMED CELLS, METHOD FOR PREPARING FACTOR IX AND CORRESPONDING PRODUCTS OBTAINED

[75] Inventor: Pierre Meulien, Strasbourg, France

[73] Assignee: Transgene S.A., Courbevoie, France

[21] Appl. No.: 209,489

[22] Filed: Mar. 14, 1994

Related U.S. Application Data

[63] Continuation of Ser. No. 970,966, Nov. 3, 1992, which is a continuation of Ser. No. 433,276, Nov. 8, 1989.

[30] Foreign Application Priority Data

Nov. 9, 1988 [FR] France ................... 88 14635

[51] Int. Cl.⁶ ..................... C12N 15/00; C12P 21/06; C07K 14/00; C07H 21/04
[52] U.S. Cl. ................. 435/69.1; 435/172.3; 435/320.1; 530/350; 530/381; 536/23.5; 536/23.2
[58] Field of Search ................... 435/69.1, 320.1, 435/172.3; 536/23.2, 23.5; 530/350, 381

[56] References Cited

U.S. PATENT DOCUMENTS 4,760,025 7/1988 Estell .................... 435/222
4,770,999 9/1988 Kaufman .................. 435/68

OTHER PUBLICATIONS

Pavirani et al. Biotechnology 5:384, 1987.
Kurochi et al PNAS 79: 6461, 1982.
Bentley et al Cell 45: 343, 1986.
DiScipio et al Biochemistry 16(4): 698, 1977.
de la Salle et al Nature 316: 268, 1985.

Primary Examiner—Suzanne E. Ziska
Attorney, Agent, or Firm—Burns, Doane, Swecker & Mathis

[57] ABSTRACT

The present invention relates to a novel DNA sequence coding for factor IX or a similar protein, corresponding to a prosequence and to mature factor IX or the mature similar protein. According to the invention, position (−3) in the prosequence is occupied by a codon coding for valine, arginine, lysine, threonine or serine, and/or the first codon of the sequence coding for the mature protein codes for an alanine.

16 Claims, 3 Drawing Sheets

-46
TATGCAGCGCGTGAACATGATCATGGCAGAATCACCAGGCCTCATCACCATCTGCCTTTT
 m  q  r  v  n  m  i  m  a  e  s  p  g  l  i  t  i  c  l  l
                        ↓ -18

AGGATATCTACTCAGTGCTGAATGTACAGTTTTTCTTGATCATGAAAACGCCAACAAAAT
 g  y  l  l  s  a  e  c  t  v  f  l  d  h  e  n  a  n  k  i
                  ↓ +1

TCTGAATCGGCCAAAGAGGTATAATTCAGGTAAATTGGAAGAGTTTGTTCAAGGGAACCT
 l  n  r  p  k  r  y  n  s  g  k  l  e  e  f  v  q  g  n  l
       ⊙        ⊙

TGAGAGAGAATGTATGGAAGAAAAGTGTAGTTTTGAAGAAGCACGAGAAGTTTTTGAAAA
 e  r  e  c  m  e  e  k  c  s  f  e  e  a  r  e  v  f  e  n

CACTGAAAGAACAACTGAATTTTTGGAAGCAGTATGTTGATGGAGATCAGTGTGAGTCCAA
 t  e  r  t  t  e  f  w  k  q  y  v  d  g  d  q  c  e  s  n

TCCATGTTTAAATGGCGGCAGTTGCAAGGATGACATTAATTCCTATGAATGTTGGTGTCC
 p  c  l  n  g  g  s  c  k  d  d  i  n  s  y  e  c  w  c  p

CTTTGGATTTGAAGGAAAGAACTGTGAATTAGATGTAACATGTAACATTAAGAATGGCAG
 f  g  f  e  g  k  n  c  e  l  d  v  t  c  n  i  k  n  g  r

ATGCGAGCAGTTTTGTAAAAATAGTGCTGATAACAAGGTGGTTTGCTCCTGTACTGAGGG
 c  e  q  f  c  k  n  s  a  d  n  k  v  v  c  s  c  t  e  g

ATATCGACTTGCAGAAAACCAGAAGTCCTGTGAACCAGCAGTGCCATTTCCATGTGGAAG
 y  r  l  a  e  n  q  k  s  c  e  p  a  v  p  f  p  c  g  r

AGTTTCTGTTTCACAAACTTCTAAGCTCACCCGTGCTGAGACTGTTTTTCCTGATGTGGA
 v  s  v  s  q  t  s  k  l  t  r  a  e  t  v  f  p  d  v  d

CTATGTAAATTCTACTGAAGCTGAAACCATTTTGGATAACATCACTCAAAGCACCCAATC
 y  v  n  s  t  e  a  e  t  i  l  d  n  i  t  q  s  t  q  s

ATTTAATGACTTCACTCGGGTTGTTGGTGGAGAAGATGCCAAACCAGGTCAATTCCCTTG
 f  n  d  f  t  r  v  v  g  g  e  d  a  k  p  g  q  f  p  w

GCAGGTTGTTTTGAATGGTAAAGTTGATGCATTCTGTGGAGGCTCTATCGTTAATGAAAA
 q  v  v  l  n  g  k  v  d  a  f  c  g  g  s  i  v  n  e  k

FIG. 1

```
ATGGATTGTAACTGCTGCCCACTGTGTTGAAACTGGTGTTAAAATTACAGTTGTCGCAGG
 w  i  v  t  a  a  h  c  v  e  t  g  v  k  i  t  v  v  a  g

TGAACATAATATTGAGGAGACAGAACATACAGAGCAAAAGCGAAATGTGATTCGAATTAT
 e  h  n  i  e  e  t  e  h  t  e  q  k  r  n  v  i  r  i  i

TCCTCACCACAACTACAATGCAGCTATTAATAAGTACAACCATGACATTGCCCTTCTGGA
 p  h  h  n  y  n  a  a  i  n  k  y  n  h  d  i  a  l  l  e

ACTGGACGAACCCTTAGTGCTAAACAGCTACGTTACACCTATTTGCATTGCTGACAAGGA
 l  d  e  p  l  v  l  n  s  y  v  t  p  i  c  i  a  d  k  e

ATACACGAACATCTTCCTCAAATTTGGATCTGGCTATGTAAGTGGCTGGGGAAGAGTCTT
 y  t  n  i  f  l  k  f  g  s  g  y  v  s  g  w  g  r  v  f

CCACAAAGGGAGATCAGCTTTAGTTCTTCAGTACCTTAGAGTTCCACTTGTTGACCGAGC
 h  k  g  r  s  a  l  v  l  q  y  l  r  v  p  l  v  d  r  a

CACATGTCTTCGATCTACAAAGTTCACCATCTATAACAACATGTTCTGTGCTGGCTTCCA
 t  c  l  r  s  t  k  f  t  i  y  n  n  m  f  c  a  g  f  h

TGAAGGAGGTAGAGATTCATGTCAAGGAGATAGTGGGGGACCCCATGTTACTGAAGTGGA
 e  g  g  r  d  s  c  q  g  d  s  g  g  p  h  v  t  e  v  e

AGGGACCAGTTTCTTAACTGGAATTATTAGCTGGGGTGAAGAGTGTGCAATGAAAGGCAA
 g  t  s  f  l  t  g  i  i  s  w  g  e  e  c  a  m  k  g  k

ATATGGAATATATACCAAGGTATCCCGGTATGTCAACTGGATTAAGGAAAAAACAAAGCT
 y  g  i  y  t  k  v  s  r  y  v  n  w  i  k  e  k  t  k  l

CACTTAATG
 t  .  .
   stop
```

FIG. 1A

DNA SEQUENCE CODING FOR HUMAN FACTOR IX OR A SIMILAR PROTEIN, EXPRESSION VECTOR, TRANSFORMED CELLS, METHOD FOR PREPARING FACTOR IX AND CORRESPONDING PRODUCTS OBTAINED

This application is a continuation of application Ser. No. 07/970,966, filed Nov. 3, 1992, now abandoned, which is a file wrapper continuation of Ser. No. 07/433,276, filed Nov. 8, 1989, now abandoned.

The present invention relates to a novel DNA sequence coding for human factor IX or a similar protein, usable for its expression in a host cell, especially a vertebrate cell and in particular a mammalian cell.

Factor IX is a vitamin K-dependent protein which participates in blood coagulation. It is synthesized in the form of a zymogen and undergoes three types of post-translational modifications before being secreted into the blood: vitamin-K-dependent conversion of glutamic acids to carboxyglutamic acids, addition of hydrocarbon chains and β-hydroxylation of an aspartic acid. In man, the liver is the site of factor IX synthesis. This protein participates in the blood coagulation cycle and is used for the treatment of hemophilia B patients. At the present time the only commercially available source of factor IX is human plasma.

However, factor IX preparations obtained by extraction from plasma may be pyrogenic, and they also entail risks of contamination with pathogenic agents or with viruses, in particular hepatitis virus or AIDS vector agents.

For this reason, it is especially advantageous to develop means for preparing factor IX of very high purity and which do not involve extraction from human or animal plasma.

For the past few years, attempts have hence been made to prepare factor IX using recombinant DNA techniques.

In particular, in earlier patent applications, the European Patent Publications EP 0,167,420, EP 0,162,782 and EP 0,251,874, the Applicant has described methods enabling host cells to be transformed in order to render them capable of producing factor IX.

Among all the host cells considered, mammalian cells gave the most advantageous results, in agreement with the findings which could be expected from the results already obtained for the expression of other vitamin K-dependent proteins. For example, the expression of factor VII or of protein C in mammalian cells was successful, leading to the production of fully active proteins (Berkner K. et al. Cold Spring Harbor: Symposia on quantitative Biology vol LI 1986).

However, the specificity of factor IX, and the difficulty of obtaining a product which is both active and produced in a sufficient yield to envisage an industrial development at a cost which is not prohibitive, were rapidly observed.

A recent publication (Rees D. J. G et al., Embo J.; 1988 7, 2053) thus describes the production of very active factor IX from dog kidney (MDCK) cells, but the level of expression is extremely low, of the order of 0.2 to 0.3 µg/10⁶ cells/24 hours. It could be observed that, at these low levels of expression, the carboxylation reaction, essential for endowing factor IX with its activity, is not saturated, thereby explaining the very large specific activity observed.

The structure of the primary translation product of factor IX cDNA is, moreover, well known, and can be divided into 3 domains: at the N-terminal end, there is a signal sequence of 28 amino acids which is cleaved when the primary translation product passes through the membrane of the endoplasmic reticulum. Next, there is a prosequence of 18 amino acids which directs the carboxylation of the 12 glutamic acids, and then the sequence coding for the mature factor IX. Recent works showed that two elements were essential for endowing factor IX with its biological activity: on the one hand the vitamin K-dependent carboxylation, and on the other hand cleavage of the prosequence when the factor IX is secreted outside the cell.

The present invention hence aims, in the light of recent scientific data on the mechanisms of maturation of factor IX in liver cells, to solve the problems encountered in the previous attempts at preparing factor IX by genetic engineering, and especially to provide means for preparing, at a level of expression compatible with an industrial exploitation, human factor IX or a similar protein which is biologically active.

The present invention relates to a DNA sequence coding for human factor IX or a similar protein, comprising at least two portions, one coding for a prosequence and the other for mature factor IX or the mature similar protein, wherein, in the portion coding for the prosequence, the codon (−3) codes for valine, arginine, lysine, threonine or serine.

In the subsequent description, codons numbered negatively correspond to the prosequence and the first codon coding for amino acid of mature factor IX is designated +1.

In particular, the preferred structure in the vicinity of the codon (−3) corresponds to the following amino acid sequence:

-X-Lys-Arg- (−3) (−2) (−1)

where X is selected from Val, Arg, Lys, Thr and Ser.

Generally speaking, "protein similar to human factor IX" in the description will be understood to denote a protein which is of similar structure while having the same type of biological activity in vivo, that is to say, for example, a protein having the same primary structure as factor IX with, if desired, a few modifications in respect of a limited number of amino acids, or else a protein not having exactly the same post-translational modifications as factor IX, or alternatively the same type of protein containing deletions in the non-essential portions.

The subject of the invention is, in particular, a novel DNA sequence coding for human factor IX or a similar protein as described above, which sequence, compared with the nucleotide sequence of factor IX cDNA shown in FIG. 1, contains the mutation of at least one nucleotide so that, in the corresponding amino acid sequence, proline (−3) is changed to valine, arginine, lysine, threonine or serine in the prosequence.

This DNA sequence is useful for the expression of factor IX or the similar protein in a host cell. For the reasons stated above, the preferred host cells are vertebrate cells, and in particular mammalian cells.

The primary translation product of factor IX cDNA contains, in fact, 3 domains, as pointed out above. The DNA sequence according to the invention preferably also contains a portion coding for a signal sequence, whose presence can promote the expression of the factor IX. It is not, however, essential that this portion corresponds to the natural signal sequence of the factor IX. It can be replaced, if desired, by the signal sequence of other vitamin K-dependent proteins such as factor VII or protein C.

More precisely, the sequence according to the invention contains GTG or GTA codons coding for valine in place of the CCA codon coding for proline at position (−3).

According to another aspect, the subject of the invention is novel factor IX analogs, as well as a novel DNA sequence coding for these novel analogs. The latter are (Ala¹) FIX analogs, in which FIX denotes natural or recombinant factor IX or a similar protein as defined above.

Similarly, the invention relates to the DNA sequence coding for these novel analogs, wherein the 5' end of the sequence in question codes for alanine. In particular, it is a DNA sequence which, compared with the nucleotide sequence of factor IX cDNA shown in FIG. 1, contains the mutation of at least one nucleotide so that, in the corresponding amino acid sequence, tyrosine (+1) is changed to alanine.

More precisely, the sequence according to the invention contains the codons GCC or GCT coding for alanine in place of the TAT codon coding for tyrosine at position (+1).

Finally, in a third aspect, the subject of the invention is a DNA sequence coding for human factor IX or a similar protein, in which the codon (+1) codes for alanine and the codon (–3) codes for valine, arginine, lysine, threonine or serine.

Thus, preferably, the DNA sequence contains a sequence coding for:

-X-Lys-Arg-Ala- (–3) (–2) (–1) (+1)

where X is selected from Val, Arg, Lys, Thr and Ser.

In particular, the subject of the invention is a novel DNA sequence coding for human factor IX or a similar protein, which sequence, compared with the nucleotide sequence shown in FIG. 1, contains mutations so that, in the corresponding prosequence, proline (–3) is changed to valine, arginine, lysine, threonine or serine, and in the sequence coding for mature factor IX or the mature similar protein, tyrosine (+1) is changed to alanine.

The method enabling a clone carrying the factor IX gene to be prepared will not be described again in detail; reference may be made to the patent publications already mentioned, the contents of which are incorporated here by reference.

The subject of the invention is also a vector for the expression of factor IX or a similar protein in a host cell, this vector containing at least the DNA sequence according to the invention and the elements providing for the expression of said sequence in said cell.

Among usable vectors, there may be mentioned viruses of the poxvirus family, especially vaccinia virus or cowpox virus, or alternatively plasmid vectors, especially integrative vectors. The different alternatives have been described in detail in the patent applications cited, especially EP 0,162,782 and EP 0,251,874.

The host cells may be of various types while being suited to the vector employed, in particular according to whether a viral vector or a plasmid vector is used. Mammalian cells, and in particular kidney cells such as VERO cells or BHK 21 cells, are used more especially. To infect CHO cells, a vector derived from cowpox virus is used.

The cells are cultured on a suitable medium providing for their growth. After transformation or infection, the cells or the culture media are harvested and the factor IX protein or its active analog can be isolated by known protein purification techniques.

In most cases, it is important that the culturing is carried out on a medium containing vitamin K, the quantity of which can vary according to the cell cultures, but will preferablby be in an amount providing for saturation of the medium, for example between 5 and 50 µg/ml of culture medium, and will generally be of the order of 10 µg/ml.

The present invention finally relates to the factor IX obtained by carrying out the method described. In particular, its subject is the human factor IX analog in which tyrosine (+1) is changed to alanine.

Other features and advantages of the invention will become apparent during the description below, illustrated by FIGS. 1 and 2, wherein:

FIG. 1 shows the nucleotide sequence of human factor IX and the corresponding amino acid sequence.

EXAMPLE 1

Construction of Factor IX cDNAs

Figure 2:
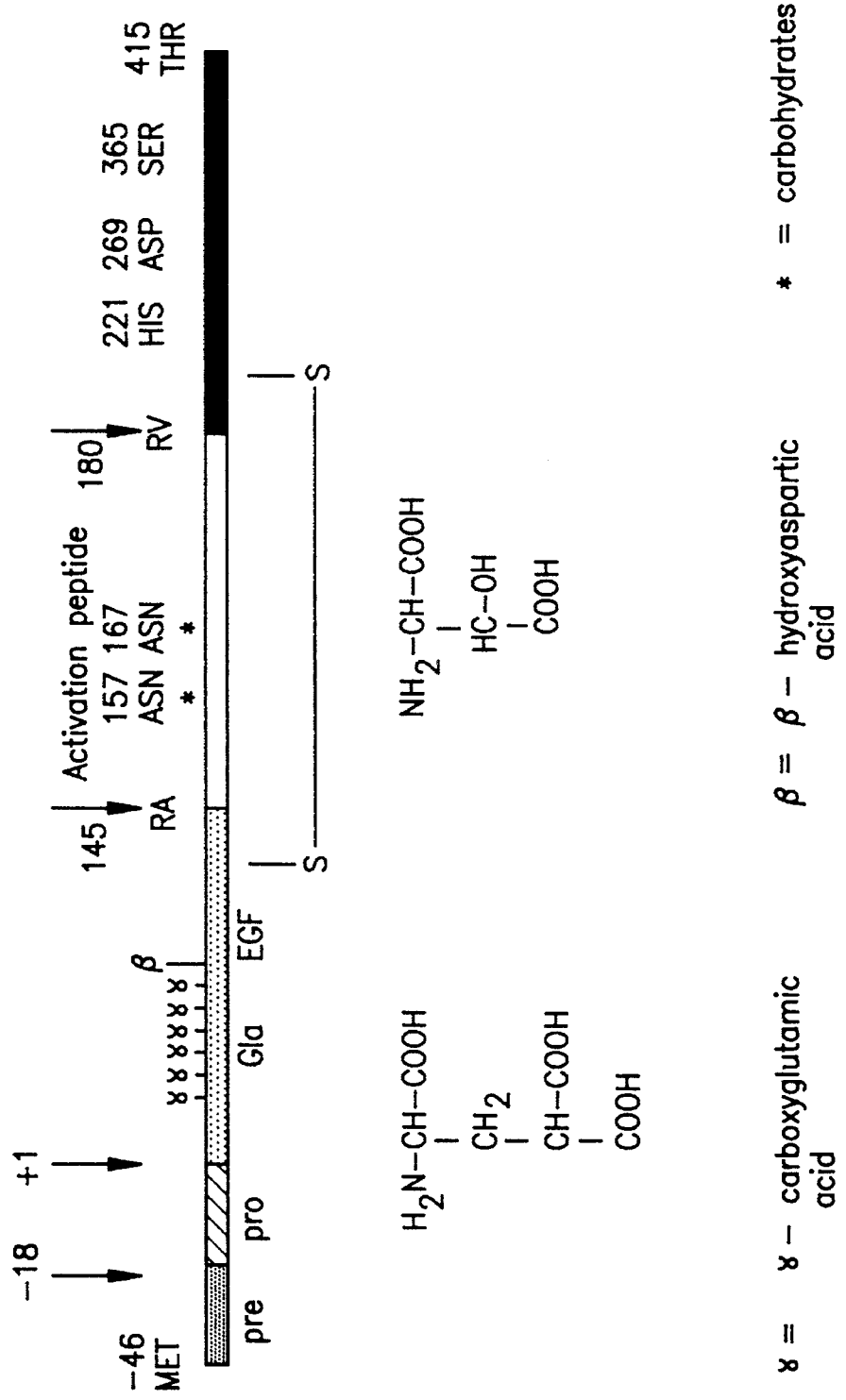
FIG. 2 shows diagrammatically the different domains of the structure of the primary translation product of the cDNA of FIG. 1.

Factor IX cDNA was cloned in the form of a Bam HI fragment into plasmid pTG 381. The construction pTG 381 was carried out in order to render the non-coding 5' end more compliant with Kozak's rules. The construction of plasmid pTG 381 is shown in the Patent Publication EP-A- 0,251,874 already cited. The Bam HI fragment is recloned into phage M13TG127, which is identical to phage M13TG131 described in Kieny et al. 1983, Gene, except that the restriction sites in the polylinker are Bgl II, Pst I, Hind III, Sma I, Bam HI and Eco RI. The novel construction in which the 5' end of factor IX cDNA is adjacent to the Sma I site is referred to as M13TG1938.

From phage M13TG1938, single-stranded DNA is prepared and mutations are carried out on the factor IX cDNA using the well-known technique of site-directed mutagenesis (Zoller and Smith Nucl. Acids Res. 1982, 10:6487, no. 20).
a) Construction of the cDNA corresponding to an amino acid sequence in which proline (–3) is changed to valine.

The synthetic oligonucleotide designated TG1771:

5'-ATACTCCTCACCCGATTCAG-3' is used.

This oligonucleotide is rapidly hybridized with the single-stranded DNA fragment at 50° C. for 30 minutes. The double-stranded molecule is then prepared by treating the hybridized mixture with polymerase Klenow fragment in the presence of deoxynucleotide triphosphate. After transformation, the molecules which have effectively undergone the desired mutations are identified by hybridization using the oligonucleotide TG1771, radioactively labeled, as a probe.

To verify that the desired mutations have indeed been introduced, the DNA sequence of the 5' end of the novel factor IX cDNA is determined. The CCA codon coding for proline is replaced by a GTG codon coding for valine.
b) Construction of the cDNA corresponding to an amino acid sequence in which tyrosine (+1) is changed to alanine.

The synthetic oligonucleotide designated TG1770:

5'-CTGAATTAGCCCTCTTTACCCGATTC-3' is used.

In this case, the TAT codon coding for tyrosine is replaced by a GCC codon coding for alanine. The conditions are identical to that described in a).
c) Construction of the cDNA corresponding to an amino acid sequence in which tyrosine (+1) is changed to alanine and proline (–3) is changed to valine.

A synthetic oligonucleotide designated TG1327:

5'-CTGAATTAGCCCTCTTACCCGATTC-3' is used.

The CCA codon coding for proline(−3) is replaced by the GTA codon coding for valine, and the TAT codon coding for tyrosine (+1) is replaced by a GCT codon coding for alanine.

EXAMPLE 2

Production of Recombinant Vaccinia Viruses and Infection of BHK21 Cells

The novel cDNAs thus prepared are excised from the M13 vector using the restriction enzyme Bam HI, and the fragments are isolated by agarose gel electrophoresis and inserted into the plasmid vector pTG186-poly, digested with Bam HI. pTG186-poly is a derivative of pTG186 whose construction is described in the patent publication EP 0,162, 782 already cited, which contains, in addition, the Bgl II-Eco RI fragment of the polylinker of phage M13TG131 already mentioned.

The three plasmids obtained:

pTG 3533 corresponding to FIX −3 val/+1 ala (oligonucleotide TG 1327)

pTG 3536 corresponding to FIX −3 val (oligonucleotide TG 1771)

pTG 3537 corresponding to FIX +1 ala (oligonucleotide TG 1770)

are inserted, respectively, into the vaccinia virus genome under the conditions described in the patent publication EP 0,162,782.

The recombinant vaccinia viruses, in which the sequences coding for factor IX are under the control of the 7.5K promoter of vaccinia, are screened for the TK⁻ phenotype using 5-bromodeoxyuridine.

The cells are cultured in MEM Glasgow medium supplemented with 5% of fetal calf serum inactivated by heating to 56° C. for 30 minutes, in the presence of 10 µg/ml of vitamin K. Infection with the recombinant viruses is performed at an infection level of 1 pfu. The cells are washed 3 times with the medium alone and then placed in contact with complete medium. 24 hours later, the presence of factor IX in the culture supernatants is tested for in two ways:

The quantity of factor IX antigen is estimated with an ELISA test (marketed by Diagnostica Stago).

The factor IX activity is calculated by measuring the coagulation time of the plasma of a hemophilic patient, supplemented with extracts (kit marketed by Stago).

The results are shown in the attached table. The quantity of factor IX antigen is expressed in µg per ml of sample.

The activity is expressed in the form of specific activity. For this purpose, the activity measurement is compared with that obtained using a mixture of normal human plasmas.

The comparative example shown in the table is the recombinant virus VVTG CII whose construction has been described in the patent publication EP-A-0,162,782, for the expression of factor IX cDNA.

It is found that, for a comparable level of expression, the specific activity is strongly enhanced, especially with the recombinant vaccinia viruses VVTG 3533 and VVTG 3537. The virus VVTG 3537 is especially advantageous since the activity of the factor IX produced is virtually 100%. The control is a normal plasma, 100% active for 5 µg/ml of FIX.

The following strains were deposited on 8th Nov. 1988 with the Collection Nationale de Cultures de Microorganismes (National Collection of Microorganism Cultures) of the Institut Pasteur (Paris):

*E. coli* pTG3537 under No. I-810
*E. coli* pTG3536 under No. I-811
*E. coli* pTG3533 under No. I-812

TABLE

QUANTITY OF FACTOR IX DETECTED IN BHK 21 CELLS INFECTED WITH THE RECOMBINANT VACCINIA VIRUSES

| Recombinant vaccinia virus | FIX Ag (µg/ml) | Specific activity (%) FIX activity/FIX Ag | Molecule obtained |
|---|---|---|---|
| VV TG C II | 2.5 | 45–55 | Natural FIX |
| VV TG 3536 | 2.0 | 50–55 | Natural FIX |
| VV TG 3533 | 1.9 | 70–85 | (Ala¹) FIX |
| VV TG 3537 | 2.3 | 80–100 | (Ala¹) FIX |

I claim:

1. A human factor IX molecule of formula $(Ala)_1 FIX$ wherein FIX refers to natural or recombinant human factor IX.

2. A DNA fragment which encodes for the human factor IX polypeptide of claim 1.

3. A DNA fragment which comprises at least:

a first portion encoding the human factor IX molecule of claim 1, and a second portion linked to the 5' end of said first portion and encoding a prosequence, which prosequence provides for carboxylation of the human factor IX molecule and is removed by cleavage upon secretion of the human factor IX molecule, which has at position −3 a valine, arginine, lysine, threonine or serine residue.

4. The DNA fragment of claim 3 wherein said prosequence is derived from the prosequence of the human factor IX precursor and differs therefrom in that the native proline at position −3 is replaced by a valine, arginine, lysine, threonine or serine residue.

5. The DNA fragment of claim 3 further comprising a third portion linked to the 5' end of said second portion and encoding a signal peptide.

6. The DNA fragment of claim 5 wherein the signal peptide is the signal peptide of the human factor IX precursor.

7. The DNA fragment of claim 5 wherein the signal peptide is a vitamin K-dependent protein signal peptide.

8. A plasmid which contains the DNA fragment of claim 2 under control of elements which provide for the expression of said DNA fragment.

9. A poxvirus vector which contains the DNA fragment of claim 2 under the control of elements providing for the expression of said DNA fragment.

10. The poxvirus vector of claim 9 which is a vaccinia virus.

11. A cell transformed by the plasmid of claim 8.

12. A cell culture infected with the viral vector of claim 9.

13. A cell which has inserted in its genome the DNA fragment of claim 2 under the control of elements providing for the expression of said DNA fragment.

14. The cell of claim 11 or 13 wherein the cell is a mammalian cell.

15. The cell culture of claim 9 wherein the cell culture is a mammalian cell culture.

16. A method for preparing $(Ala)_1 FIX$ comprising culturing the cell or cell culture of any one of claims 11, 12 or 13, and recovering $(Ala)_1 FIX$ from the culture.

* * * * *